(12) United States Patent
Howitz et al.

(10) Patent No.: US 7,114,541 B2
(45) Date of Patent: Oct. 3, 2006

(54) METHOD FOR PRODUCING A 3-D MICRO FLOW CELL AND A 3-D MICRO FLOW CELL

(75) Inventors: Steffen Howitz, Dresden (DE); Guenther Fuhr, Berlin (DE)

(73) Assignee: Gesim Gesselschaft fur Silizium-Mikrosysteme mbH, Grosserkmannsdorf (DE)

( * ) Notice: Subject to any disclaimer, the term of this patent is extended or adjusted under 35 U.S.C. 154(b) by 463 days.

(21) Appl. No.: 10/363,965

(22) PCT Filed: Sep. 3, 2001

(86) PCT No.: PCT/DE01/03324

§ 371 (c)(1),
(2), (4) Date: May 3, 2003

(87) PCT Pub. No.: WO02/21115

PCT Pub. Date: Mar. 14, 2002

(65) Prior Publication Data

US 2004/0038387 A1    Feb. 26, 2004

(30) Foreign Application Priority Data

Sep. 7, 2000  (DE) ............................ 100 44 333
Feb. 3, 2001  (DE) ............................ 101 04 957

(51) Int. Cl.
*H01S 4/00* (2006.01)
*B23P 17/04* (2006.01)
*B29C 65/00* (2006.01)
*B32B 37/00* (2006.01)
*G05G 15/00* (2006.01)

(52) U.S. Cl. ............... 156/349; 29/592; 29/592.1; 156/358; 156/359; 216/33; 422/50; 422/58; 422/68.1; 422/82.01; 422/100; 422/101; 422/102; 422/103; 422/104; 436/43

(58) Field of Classification Search .......... 29/592.1, 29/592; 156/349, 358, 359; 216/33; 422/50, 422/58, 68.1, 82.01, 100–104

See application file for complete search history.

(56) References Cited

U.S. PATENT DOCUMENTS

| | | | |
|---|---|---|---|
| 4,908,112 A | 3/1990 | Pace | 204/299 |
| 5,141,868 A | 8/1992 | Shanks et al. | 435/288 |
| 5,520,787 A | 5/1996 | Hanagan et al. | 204/409 |

(Continued)

FOREIGN PATENT DOCUMENTS

DE    3739333    6/1989

(Continued)

OTHER PUBLICATIONS

"3-D Microelectrode System for Handling and Caging Single Cells and Particles" by Muller et al.;*Biosensors & Bioelectronics, Elsevier, Science Publishers*, Barking, GB, vol. 14, Mar. 15, 1999; pp. 247-256.

(Continued)

*Primary Examiner*—Jill Warden
*Assistant Examiner*—Brian Sines
(74) *Attorney, Agent, or Firm*—Baker Botts LLP; Manu J. Tejwani

(57) ABSTRACT

A 3D micro flow cell is fabricated by forming a first spacer on a substrate to define the flow channel of the cell extending between inlet and outlet openings. A second spacer, comprising a pasty adhesive is applied outside the first spacer or in a groove on the first spacer to seal the cell when the first substrate is joined to a second substrate.

11 Claims, 4 Drawing Sheets

U.S. PATENT DOCUMENTS

| | | | |
|---|---|---|---|
| 6,045,676 A | 4/2000 | Mathies et al. | 204/603 |
| 6,890,093 B1 * | 5/2005 | Karp et al. | 366/336 |
| 6,935,772 B1 * | 8/2005 | Karp et al. | 366/341 |

FOREIGN PATENT DOCUMENTS

| | | |
|---|---|---|
| WO | 0017630 | 3/2000 |

OTHER PUBLICATIONS

"Hydrodynamic ECL (Electrogenerated Chemiluminesence)" by H. L. Jones et al., *IBM Technical Disclosure Bulletin*, Oct. 1979, vol. 22, No. 5 p. 2065.

* cited by examiner

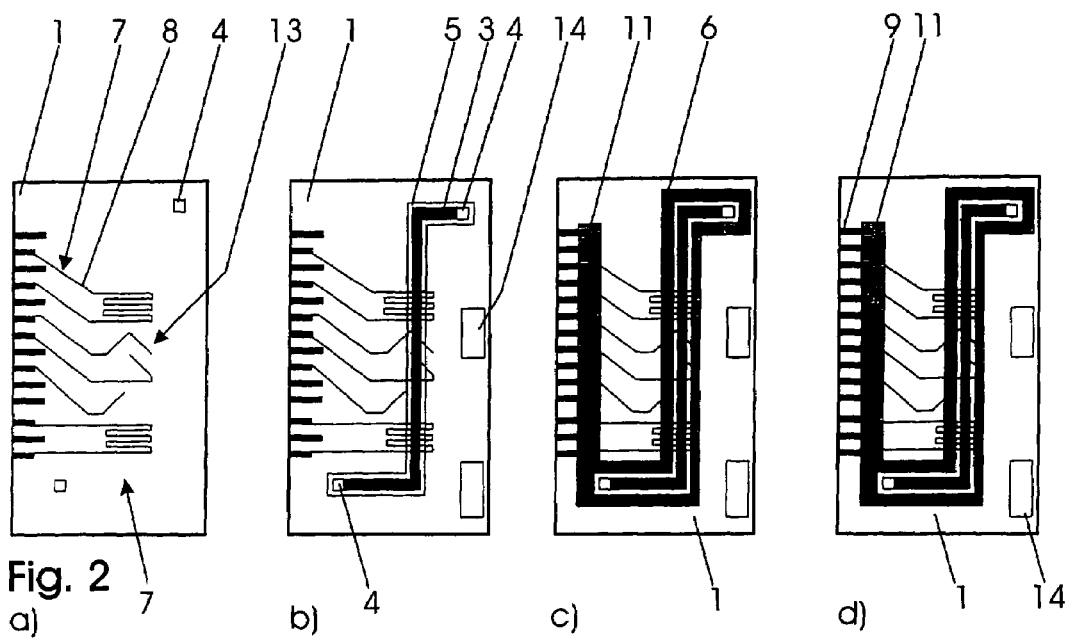
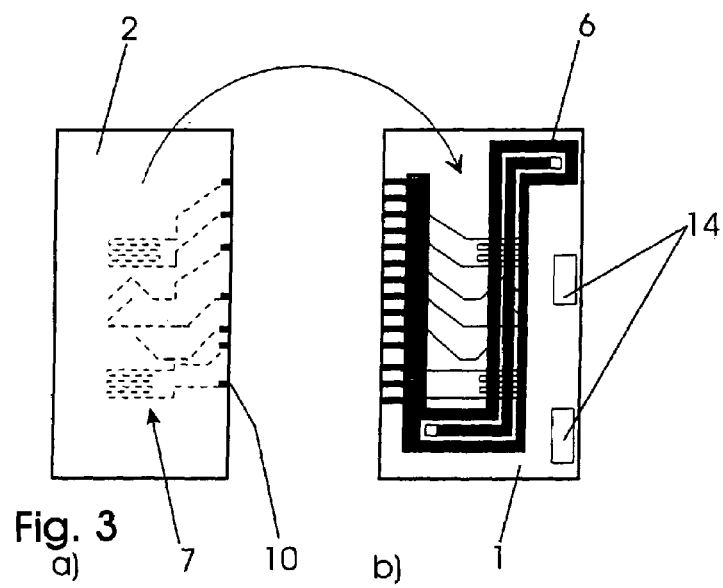
Fig. 2
Fig. 3

METHOD FOR PRODUCING A 3-D MICRO FLOW CELL AND A 3-D MICRO FLOW CELL

BACKGROUND OF INVENTION

The invention relates to a method for producing a 3D micro flow cell, consisting of a lower and an upper substrate between which is located a flow channel that is penetrated by an electrode structure connected to external contacts, wherein at least one of the substrates is equipped initially with a conductive trace and electrode structure and is provided at the ends of the flow channel with feedthroughs for connecting a fluid inlet and outlet. The invention further relates to a 3D micro flow cell produced using the method.

3D micro flow cells of this nature are used, for example, as cell manipulators for the handling and optical analysis of dielectric biological particles, in particular of cells and/or bacteria or viruses. To this end, the micro flow cells are equipped with a flow channel at the ends of which are provided one or more fluid inlets and outlets. Said fluid inlets and outlets are made by feedthroughs extending perpendicular to the flow channel, for example. The height of the fluid channel is generally in the range of a few micrometers, while the flow channel is delimited at the top and bottom by glass substrates and/or silicon substrates and at the sides by suitable channel walls. In order to be able to hold individual cells "freely suspended" at a predetermined location within the fluid channel, electrodes that generate an electrical field when a voltage is applied are located in the fluid channel. The electrostatically held cell can then be illuminated by suitable illumination and observed by means of a microscope.

A variety of technologies are generally known to make it possible to implement such three-dimensional structures. Thus, for example, a glass substrate can be wet chemical etched on one side in order to produce a flow channel therein and subsequently be joined by diffusion welding to a second glass substrate as the cover element. The requisite electrodes for handling cells or biological particles are previously applied to the first and/or second glass substrate by known photolithographic methods, and the second glass substrate is subsequently mounted face down on the bottom glass substrate.

However, the technology of diffusion welding is relatively expensive and the capabilities of generally isotropic glass structuring are limited. It can be considered a further disadvantage that only relatively coarse electrode structures can be applied to the structured glass surfaces. However, in order to be able to implement exact handling of individual cells or biological particles, an extremely precise geometric structure of the electrodes is necessary to be able to electrostatically manipulate these particles and hold them in place at the desired location in a noncontacting manner.

Another technology is described by Müller/Gradl/Howitz/Shirley/Schnelle/Fuhr in the journal "BIOSENSORS & ELECTRONICS," No. 14 (1999), pp. 247–256. Described here is the application of the purely manual epoxy resin gluing technique, wherein first a polymer spacer is processed on a glass surface that has previously been equipped with platinum electrodes and electrically conductive traces. Then the glass substrate is coated outside the polymer structure with a synthetic resin, such as epoxy resin, as an adhesive and after that a second piece of glass, which likewise has been equipped with electrodes, is positioned thereupon and the bond is subsequently compressed. This assembly step is usually performed with a so-called die bonder (chip bonder).

There are difficulties here in that it is problematic to manufacture micro flow cells that always have exactly identical geometric dimensions and in which it is certain that no adhesive penetrates into the flow channel during the assembly process, something which would partially narrow the channel. The efficiency of this step is thus extremely poor and unsuitable for mass production.

Moreover, a so-called underfill technique has become known in which a first polymer (thick lacquer) is spun onto the glass substrate that is equipped with electrodes, wherein the thickness of the spun-on polymer is predetermined by the height of the channel provided. The positive channel system is then structured from this polymer, i.e. the excess thick lacquer is completely removed during this photostructuring. The second glass substrate is then aligned with and pressed onto the first glass substrate. The 3D arrangement obtained in this manner is held by lateral penetration of a creepable adhesive (underfiller), a second polymer, after which the channel system in the first polymer is washed out again with a solvent. The solvent must not attack the second polymer here. A particular disadvantage here is that no inner flow elements can be manufactured in the channel in this way because they cannot be reached by the second polymer. Moreover, this technique is extremely time-consuming and limited with respect to structural resolution.

The object of the invention is to disclose a method for producing a 3D micro flow cell that can be implemented economically and with which especially uniform geometric parameters can be achieved. The invention further has the object of creating a 3D micro flow cell that can be produced economically with the method according to the invention.

SUMMARY OF THE INVENTION

The object of the invention is achieved with regard to a method for producing a 3D micro flow cell consisting of a lower and an upper substrate between which is located a flow channel that is penetrated by an electrode structure connected to external contacts, wherein at least one of the substrates is equipped initially with a conductive trace and electrode structure, and is provided at the ends of the flow channel with feedthroughs for connecting fluid inlets and outlets. A first spacer provided defining both sides of the channel, and additional spacing shims consisting of a substantially non-compressible or curable material of a predetermined depth, are applied at least to the lower substrate, and irreversibly fixed to the lower or upper substrate once applied. A pasty adhesive is applied with a uniform thickness as a second spacer outside of the flow channel, and in that the upper substrate is subsequently positioned on the lower substrate and joined thereto by the action of force and heat, thus simultaneously sealing the flow channel.

This simple to implement method ensures extreme precision of the geometric dimensions of the flow channel on the one hand, and full and simple sealing of the channel on the other hand, without the risk of amounts of adhesive penetrating the flow channel, which could narrow it.

In a first refinement of the invention, the second spacer is applied directly next to the first spacer, parallel to and surrounding it, wherein the thickness of the second spacer prior to assembly is greater than the height of the first spacer.

In a special variant of the invention, the first spacer is provided with a groove running along it, and the pasty second spacer is dispensed or printed in the groove. As a result of this version, penetration of adhesive (second spacer) into the flow channel when the upper substrate is placed on the lower substrate and during the subsequent compression is reliably prevented. Moreover, even relatively large spacer heights can be achieved without problem.

The shallow groove can be produced with the usual photolithographic means.

There are various possibilities for producing the first spacer and the shims. Thus, the first spacer and the distance pieces can be applied to the lower substrate by screen printing or dispensing and subsequently cured, with the curing accomplished by the action of heat or by irradiation with light or UV, for example.

Another possibility consists in that the first spacer and the shims are produced on the lower substrate by means of a photolithographic method and then cured through tempering. To this end, preferably the first spacer and the shims are made of a photostructurable resist, wherein the remaining thickness defines the height of the flow channel. Photolithographic methods permit reduced edge roughness as compared to screen printing, and thus greater precision, so that finer structures can be produced.

Another possibility consists in that the first spacer and the shims are made of a prestructured metal or polymer film that is adhesive at least on one side and affixed to the lower substrate.

An adhesive based on epoxy resin or silicone rubber is preferably used as the second spacer to fasten the upper substrate to the lower substrate, i.e. to produce the 3D structure. The bond between the upper and lower substrate can be produced under the action of pressure and heat and/or light or UV irradiation.

The object of the invention is further attained by a 3D micro flow cell consisting of a lower and an upper substrate wherein located between the substrates is a flow channel that is provided with fluidic feedthroughs and is penetrated by an electrode structure connected to external contacts, characterized in that arranged at least on the one substrate are a first spacer defining the flow channel, and additional shims consisting of a substantially non-compressible or curable material of a predetermined thickness, that are irreversibly fixed to one of the substrates, and in that the other substrate is joined to the first substrate, tightly sealing the flow channel, by means of a pasty, curable adhesive layer forming a second spacer.

In a first embodiment of the invention, the second spacer extends outside the flow channel on both sides on the outer side of the first spacer, parallel to and surrounding the latter.

In a second embodiment of the invention, a shallow groove for accommodating a pasty second spacer is incorporated in the surface of the first spacer, by which means the penetration of adhesive into the flow channel during the process of assembling the upper substrate onto the lower substrate is reliably prevented.

The thickness of the first spacer and the shims must be equal and should be between 10 µm and 1 mm, depending on the intended height of the flow channel.

In a refinement of the invention, at least one of the two glass substrates can have a thickness from 250 µm to 1000 µm and the other can be from 500 µm to 1000 µm thick. In this way, the composite possesses sufficient mechanical stability and at the same time is suitable for use in high resolution microscopy.

The upper substrate can also consist of a plastic film, for example a polymer film, with a thickness from 170 µm to 200 µm.

Another embodiment of the invention is characterized in that the region of the flow channel is optically transparent at least in the wavelength range from 250 nm to 450 nm. This can be achieved simply through the selection of suitable materials for the upper and lower substrates.

In another special embodiment, the invention is characterized in that at least one of the upper or the lower substrates has metallic microelectrodes that stand in a predetermined three-dimensional geometrical relationship to one another and in that the upper substrate is mounted face down on the lower substrate. The microelectrodes of the upper substrate are equipped with contact pads and are electrically connected to the external contacts on the lower substrate by conductive adhesive, conductive rubber, or solder pads.

The microelectrodes can consist of a thin film system, of platinum, gold, tantalum, titanium, aluminum, or a conductive ITO (indium tin oxide).

In a special embodiment of the invention, the electrode and connection system on the upper and lower substrates is insulated over its entire area by means of an inorganic insulating material, where the insulating material is omitted in the interior of the flow channel, on the contact pads, and on the contact supports in order to permit adequate electrical contact at these locations.

In order to mask fluorescence of the polymer of the first spacer—which forms the flow channel—resulting from light excitation during optical microscopic detection, an opaque mask may be applied to the outside of the upper substrate in such a manner that at least the edge region of the flow channel is covered, but its central region is left clear. The particular advantage of such a mask is that fluorescence-based detection of biological cells in the flow channel can take place without the possibility of the fluorescence that is simultaneously produced by the materials that delimit the flow channel exerting a disruptive influence.

The mask can advantageously also be designed as internal and external shielding for electromagnetic and bioelectric waves, thus reliably preventing any incident electromagnetic radiation from exerting a negative effect on the cells themselves and thus on the result of the detection.

In the simplest case, the mask consists of metal, which can also consist of a photolithographically structurable thin film, for example of Cu or Al.

It is useful for the thin film to be removable so that the entire width of the flow channel can be optically examined when needed.

In a special refinement of the invention, in order to prevent the formation of an adhesive film on the inside of the flow channel insofar as possible, the contact surface of the first spacer is provided with a slot or other type of recess extending along its length to accommodate adhesive during the assembly process.

In special cases, it can be desirable for the upper substrate to be removably bonded to the lower substrate. For this case, a special variant of the invention is characterized in that the first spacer consists of a photoresist and the second spacer of a printed silicone rubber, and after full vulcanization, the upper and lower substrates are joined together frictionally, reversibly, and so as to be fluid tight. In this way, the 3D micro flow cell can be opened again after use and sterilized when needed.

Another special variant of the invention is characterized in that the first spacer is photolithographically produced on the lower substrate and has a width that substantially corresponds to the parallel separation of first spacer and second spacer and in that the upper substrate is attached to the lower substrate through adhesive force. However, this variant of the invention is only suitable for cases in which the upper substrate does not contain an electrode structure.

The invention is explained in detail below with an exemplary embodiment.

BRIEF DESCRIPTION OF THE DRAWINGS

FIG. 2 shows a sequence of manufacture of the lower substrate of the 3D micro flow cell.

FIG. 3 shows the assembly sequence for completion of the 3D micro flow cell.

DESCRIPTION OF THE INVENTION

Figure 1:
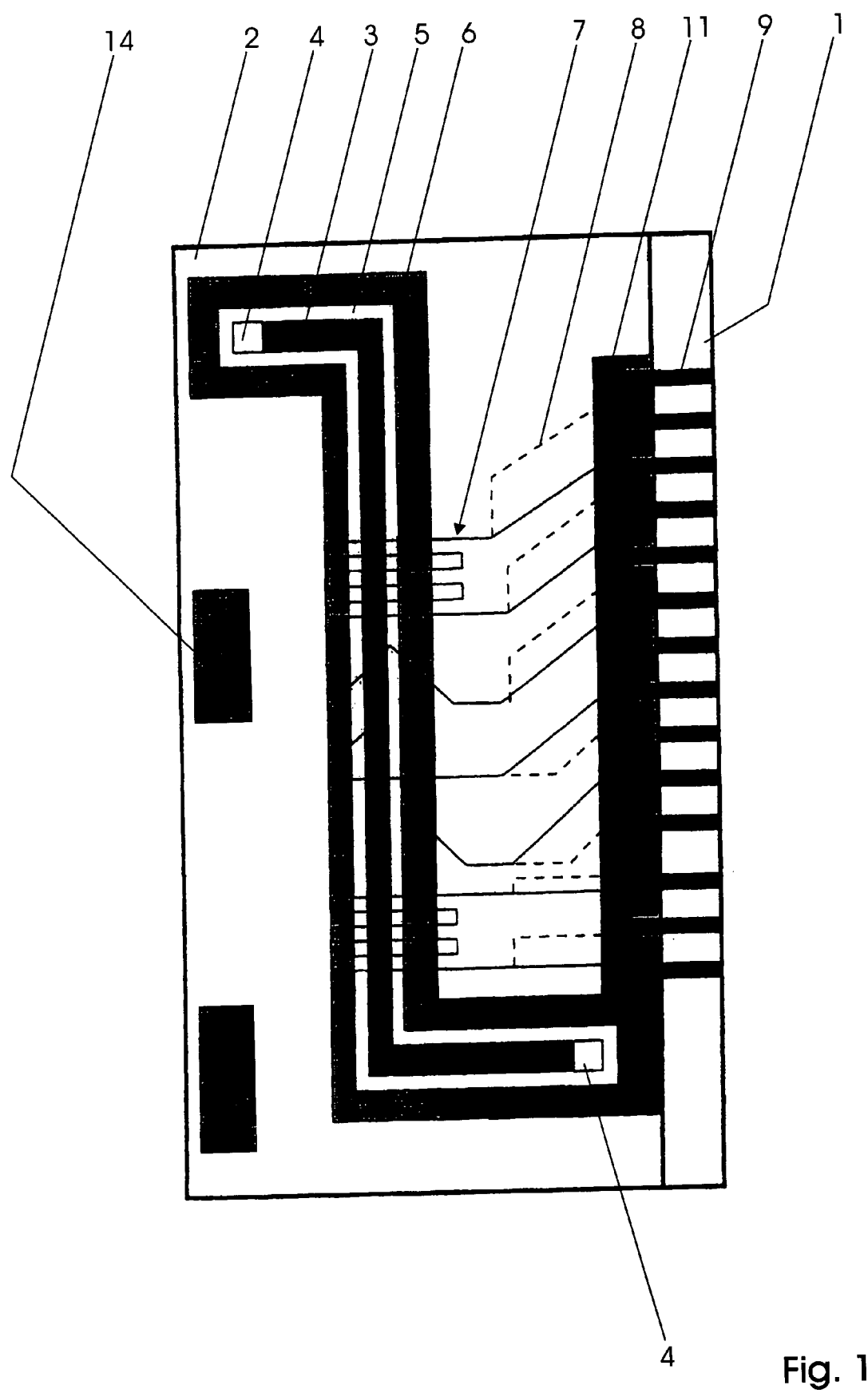
FIG. 1 is a schematic top view of a 3D micro flow cell.

Seen in FIG. 1 is a 3D micro flow cell in accordance with the invention that consists of a lower substrate 1 made of glass with a thickness of approximately 750 µm and an upper substrate 2. In the present case, the upper substrate is likewise made of glass with a thickness of approximately 150 µm, although other materials that have adequate transparency in the wavelength range from 250–450 nm can also be used here. Located between the two substrates 1 and 2 is a flow channel 3 that is provided at each end with a fluidic feedthrough 4 for inlet and outlet of a fluid. The flow channel 3 is delimited laterally over its entire length by a first spacer 5 and an additional second spacer 6, which extends outside the flow channel 3 on both sides next to the first spacer.

Moreover, an electrode structure 7 that is connected to external contacts 9 via conductive traces 8 is located on the upper substrate 2 and the lower substrate 1.

Figure 5:
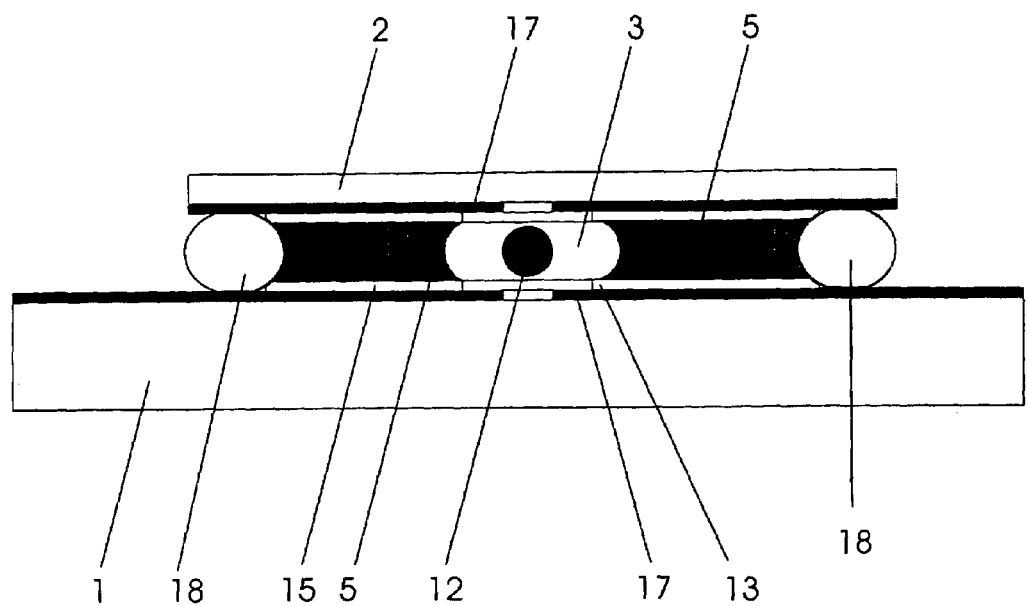
FIG. 5 is a sectional view of a 3D micro flow cell with flip chip contacts.

In contrast to the conductive traces 8 on the lower substrate 1, the conductive traces 8 on the upper substrate 2 end in contact pads 10, which are electrically connected to the external contacts 9 on the lower substrate 1 by means of conductive adhesive or solder pads or micro solder balls (micro balls) 18 (FIG. 5).

In addition, all external contacts 9 on the lower substrate 1 are combined in a contact support 11 whose purpose is additional mutual insulation.

To electrostatically hold cells 12 or biological particles or the like at a predetermined location within the flow channel 3 (cf. FIG. 5), the electrode structure 7 contains microelectrodes 13, which extend into the flow channel on the lower substrate 1 or the upper substrate 2 as applicable, and are exactly positioned in three dimensions.

Spacing shims 14 are also provided, moreover, in order to achieve a spacer distance between the substrates 1, 2 that is constant over the substrate.

In order to better illustrate the design of the individual structures on the lower substrate 1, FIG. 2 shows a suitable sequence. To this end, the lower glass substrate 1 is first bored in order to be able to later implement the necessary fluidic feedthroughs 4 to the flow channel 3. The lower substrate 1 is then provided with the electrode structure 7 and the conductive traces 8 as well as the external contacts 9 by means of conventional thin film techniques and photolithography. The entire structure is then insulated over its entire surface with an inorganic insulating material 15 (FIG. 5). The insulator 15 is then removed in the region of the future flow channel 3 and at the external contacts 9 in order to be able to produce effective electrical structures.

Subsequently, the flow channel 3 is formed on the lower substrate 1 in that a first spacer 5 made of a polymer, is applied to the lower substrate 1. Of course, the first spacer can alternately be formed on the upper substrate 2. A high-viscosity positive photoresist, a negative dry resist, or a polymer film applied by screen printing can be used to produce the first spacer 5. All three variants allow the manufacture of a first spacer 5 that can have a thickness in the range of 10 µm to 100 µm. It is important in each case that the thickness of the spacer 5 also determines the height of the flow channel 3.

Next, the first spacer 5 is cured through the action of heat or UV radiation. It is extremely important in this step that after curing, the first spacer 5 has the precise thickness that the flow channel 3 should later have.

After that, the second spacer 6, surrounding the first spacer 5, is applied to the lower substrate 1 by printing or with the use of a dispenser. The thickness of the second spacer 6 is greater than that of the first spacer 5. An adhesive based on epoxy resin or silicone rubber is used as the second spacer 6 in any event.

It is also possible to form in the surface of the first spacer a shallow groove 19 (FIG. 6) running along it using known photolithographic methods and to dispense or print the second spacer (adhesive) therein. The depth of the groove is between 10–35 µm.

The upper and lower substrates 1, 2 are then glued in an aligned position.

The advantage of this variant is that sandwich systems with significantly greater spacer heights over 20–50 µm can also be implemented.

For the upper substrate 2 shown in FIG. 3a, only an electrode structure 7 is produced in the same manner as on the lower substrate and is connected to contact pads 10 via conductive traces. This structure as well is subsequently insulated over its entire surface with an organic or inorganic insulating material 15, with the electrode structure 7 in the region of the future flow channel and the contact pads 10 being subsequently exposed again by removal of the insulating material 15.

Figure 4:
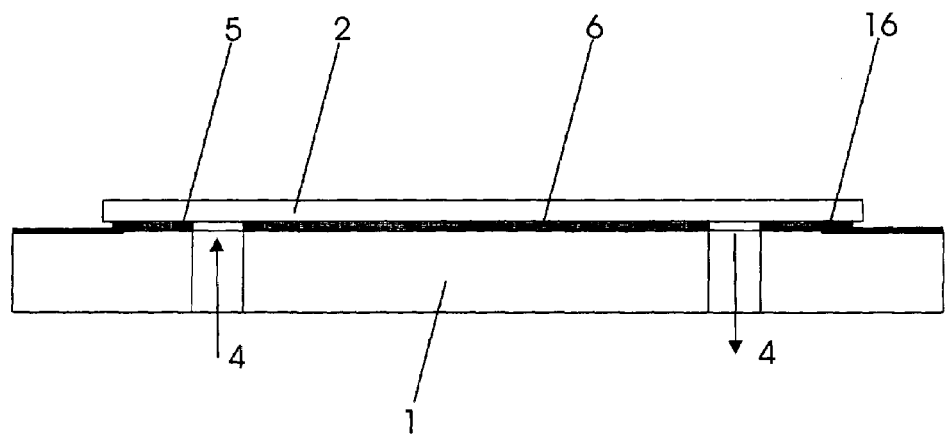
FIG. 4 is a sectional view of FIG. 3 the 3D micro flow cell as a glass/glass module.

Flip chip assembly takes place next as shown in FIG. 3, in that the upper substrate 2 is positioned face down exactly over the lower substrate and is then placed on it. Heat is supplied at the same time to cure the second spacer 6 and thus create the 3D structure shown in FIGS. 1, 4, and 5.

In order to be able to produce the necessary electrical contacts between the contact pads 10 on the upper substrate and the external contacts 9 on the lower substrate, a suitable conductive adhesive 16 is dispensed on the connections prior to flip chip assembly.

To prevent adhesive from penetrating the flow channel 3 during the assembly process, there can be incorporated in the surface of the first spacer 5, a slot or groove, 19 which may be V-shaped, extending along the length of the same. This can be done without difficulty using known methods of photolithography. Moreover, a higher strength of the overall structure is achieved in this way.

Since the channel walls of the first spacer 5 generate a disruptive fluorescence when a cell 12 that is spatially held in place in the flow channel 3 is illuminated during optical detection, suitable masking of the fluorescence of the spacer material is helpful place for high-resolution optical detection, for example using an immersion objective of a microscope.

Figure 6:
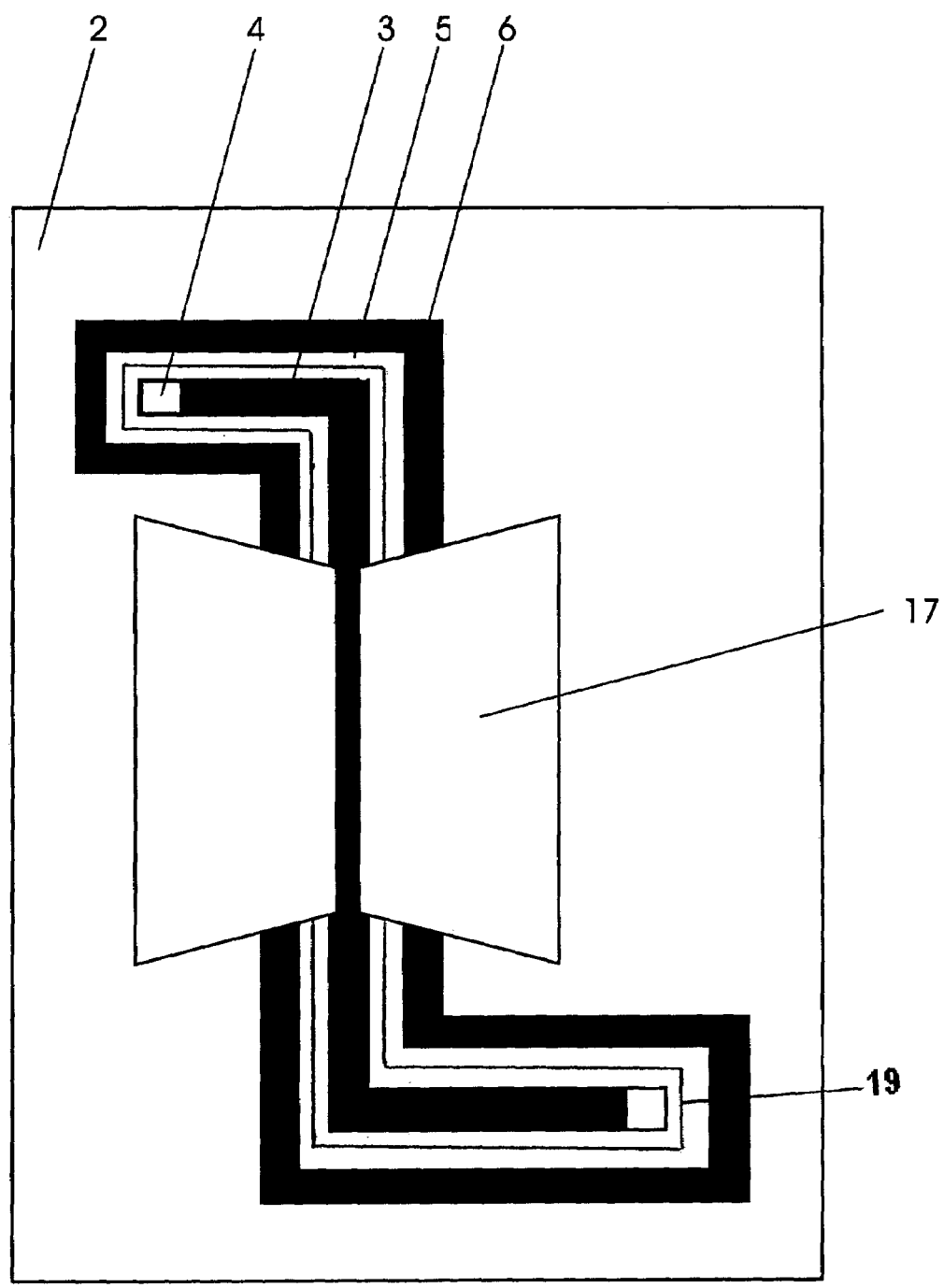
FIG. 6 shows a 3D micro flow cell equipped with a Cu mask.

In order to preclude such interference, an opaque mask 17 as shown in FIG. 6 can be provided that covers the edge of the flow channel 3 and leaves the central region of the flow channel clear. Mask 17 can be made of a metallic structurable and aligned thin film. In order to make such a mask reversible if needed, the use of an easily removable layer system is beneficial so that the entire cross-section of the flow channel 3 can be observed as needed.

The particular advantage of a mask 17 is that fluorescence-based detection of biological cells 12 in the flow channel 3 can take place without the possibility of the fluorescence that is simultaneously produced by the materials that delimit the flow channel 3 exerting a disruptive influence brought about by scattered light. It can be considered a further advantage that, as a result of the mask 17, it is no longer necessary to provide an additional mask in the optical system, which results in higher light intensity of the optical system.

The mask 17 can advantageously also be designed as internal and external shielding for electromagnetic and bioelectric radiation, thus reliably preventing normally present electromagnetic interference from exerting a negative effect on detection of the cells.

In the simplest case, the mask 17 can be made of a metal, where the mask 17 can also consist of a photolithographically structurable thin film, for example of Cu, Al or another metal.

In this way, the mask 17 can be removed simply through etching without harming the micro flow cell.

In the event that only optical shielding by the mask 17 is important, the mask can of course be manufactured of other materials, for example a plastic.

In special cases, it can be desirable for the upper substrate 1 to be removably joined to the lower substrate 2. For this case, a special variant of the invention is characterized in that the second spacer 6 of silicone rubber is imprinted on the first spacer 5, and after full vulcanization the upper and lower substrates 2, 1 are joined together frictionally. The frictional connection can be implemented with a simple clamping arrangement.

In the simplest case, i.e. when the upper substrate contains no electrode structure 7, a substantial simplification of the structure of the 3D micro flow cell can be achieved if the first spacer 5 that has been photolithographically produced on the lower substrate 1 has a width that substantially corresponds to the parallel separation of first spacer 5 and second spacer 6 (FIG. 5), wherein the upper substrate 2 is attached to the lower substrate 1 merely through adhesive force. A prequisite here is that the contact surface of the first space 5 must be completely even with the upper substrate.

While there have been described what are believed to be the preferred embodiments of the present invention, those skilled in the art will recognize that other and further changes and modifications may be made thereto without departing from the spirit of the invention, and it is intended to claim all such changes and modifications that fall within the truse scope of the invention.

We claim:

1. A method of producing a 3D micro flow cell having a flow channel arranged between an upper and a lower substrate and connected to inlet and outlet fluid passages, wherein at least one of said substrates includes electrode structure having external electrical connections, comprising:
   applying a first spacer defining opposite sides of said flow channel and permanently fixed to a first substrate;
   applying non-compressible shims on at least one of said substrates to define a separation of said substrates;
   applying a second spacer comprising a pasty adhesive with uniform thickness to one of said substrates, said second spacer being formed outside of said flow channel; and
   positioning a second substrate over said first substrate and joining said substrates by applying one of force and heat to seal said flow channel.

2. A method as specified in claim 1 wherein said second spacer is applied directly next to, parallel to and surrounding said first spacer, and wherein prior to said positioning, said first spacer has a thickness greater than a thickness of said first spacer.

3. A method as specified in claim 1, wherein a shallow groove is provided extending along the length of said first spacer and wherein said second spacer is applied in said groove.

4. A method as specified in claim 3 wherein said shallow groove is applied by photolithographic methods.

5. A method as specified in claim 1 wherein said first spacer and said shims are applied by screen printing and subsequently cured.

6. A method as specified in claim 4 wherein said curing is accomplished by one of heating and irradiation with light.

7. A method as specified in claim 1 wherein said first spacer and said shims are applied by one of photolithographic methods and dispensing, and cured by tempering.

8. A method as specified in claim 7 wherein said first spacer and shims are made of a photostructurable resist having a thickness which defines the height of the flow channel.

9. A method as specified in claim 1 wherein said first spacer and said shims are made of a prestructured film that is adhesive at least on one side and affixed to a substrate.

10. A method as specified in claim 1 wherein a bond between said upper substrate and said lower substrate is produced under the action of pressure and one of heat and UV irradiation.

11. A method as specified in claim 1 wherein said second spacer is formed from a material selected from an adhesive based on epoxy resin and silicone rubber.

* * * * *